United States Patent
Watson et al.

(10) Patent No.: US 11,169,001 B2
(45) Date of Patent: Nov. 9, 2021

(54) MAGNETIC-BASED MOTION MONITORING FOR TWO OBJECTS SHARING COMMON JOINT

(71) Applicant: College of William & Mary, Williamsburg, VA (US)

(72) Inventors: Amanda Watson, Williamsburg, VA (US); Andrew Lyubovsky, Williamsburg, VA (US); Gang Zhou, Williamsburg, VA (US)

(73) Assignee: College of William & Mary, Williamsburg, VA (US)

( * ) Notice: Subject to any disclaimer, the term of this patent is extended or adjusted under 35 U.S.C. 154(b) by 192 days.

(21) Appl. No.: 16/743,502

(22) Filed: Jan. 15, 2020

(65) Prior Publication Data

US 2021/0215508 A1 Jul. 15, 2021

(51) Int. Cl.
*G01D 5/14* (2006.01)
*A61B 5/11* (2006.01)
*G01B 7/30* (2006.01)

(52) U.S. Cl.
CPC .............. *G01D 5/14* (2013.01); *A61B 5/1126* (2013.01); *A61B 2562/0223* (2013.01); *G01B 7/30* (2013.01)

(58) Field of Classification Search
CPC . G01D 5/14; A62B 5/1126; A62B 2562/0223; G01B 7/30
See application file for complete search history.

(56) References Cited

U.S. PATENT DOCUMENTS

| | | | | |
|---|---|---|---|---|
| 6,104,379 A * | 8/2000 | Petrich | .................... | G06F 3/014 345/156 |
| 9,652,038 B2 * | 5/2017 | Osman | .................... | G06F 3/014 |
| 9,665,174 B2 * | 5/2017 | Osman | .................... | H04N 5/225 |
| 10,055,019 B2 * | 8/2018 | Beran | .................... | A63F 13/577 |
| 2017/0336832 A1 * | 11/2017 | Furlong | ................ | G01D 5/145 |

* cited by examiner

*Primary Examiner* — Walter L Lindsay, Jr.
*Assistant Examiner* — Milton Gonzalez
(74) *Attorney, Agent, or Firm* — Jason P. McDevitt

(57) ABSTRACT

A method is provided for monitoring relative positions of two objects sharing a common joint during motion between the two objects. An electromagnet is positioned on a first object and a magnetic sensor is positioned on a second object. The electromagnet's power or polarity is cycled during a monitoring session in accordance with a periodic schedule of alternating power-on/power-off periods or alternating-polarity periods, respectively. The magnetic sensor's output during one or more of the power-off periods or the alternating-polarity periods is used to remove environmental magnetic interference to dynamically determine the distance between the electromagnet and the magnetic sensor where the determined distance and the north pole orientation of the electromagnet are indicative of relative positions of the first object and the second object.

32 Claims, 4 Drawing Sheets

MAGNETIC-BASED MOTION MONITORING FOR TWO OBJECTS SHARING COMMON JOINT

STATEMENT REGARDING FEDERALLY SPONSORED RESEARCH AND DEVELOPMENT

This invention was made with government support under Grant No. NSF CNS-1841129 awarded by the National Science Foundation. The government has certain rights in the invention.

FIELD OF INVENTION

The field of the invention relates generally to magnetic-based monitoring systems and methods, and more particularly to a magnetic-based method and system for monitoring motion between two objects that share, and are manipulated about, a common joint.

BACKGROUND OF THE INVENTION

Monitoring the motion of objects or living beings has traditionally been accomplished by some type of visual or image-based device. For example, video recordings of a patient's anatomical movements are frequently used to evaluate degrees of flexion and extension during patient treatment and/or rehabilitation. Unfortunately, video recordings do not provide sufficient details when anatomical movements are very fast and/or complex, e.g., a pitcher's throwing motion, a volleyball player's spiking motion, a soccer or football player's kicking motion, a tennis player's serving motion, etc. A common feature of these examples is that the fast and/or complex motion of two body parts are manipulated about a common joint.

To address drawbacks of video recordings, a variety of magnetic-based motion monitoring systems have been developed. Unfortunately, local magnetic fields (e.g., Earth's magnetic field and magnetic fields due to local structures and/or equipment) present in a monitoring environment can corrupt magnetically sensed data. This is especially true when a person or object being monitored is mobile, will move in their environment, and/or will need to be monitored in terms of the presence of magnetic anomalies.

BRIEF SUMMARY OF THE INVENTION

Accordingly, it is an object of the present invention to provide a method for monitoring relative position of two objects sharing a common joint during motion between the two objects.

Another object of the present invention is to provide a method for monitoring fast motion between two objects sharing a common joint.

Still another object of the present invention is to provide a magnetic-based motion monitoring system that eliminates data corruption due to local magnetic fields.

In accordance with an embodiment of the present invention, a method is provided for monitoring relative positions of two objects sharing a common joint during motion between the two objects. The joint is one that supports relative motion between a first object coupled to the joint and a second object coupled to the joint. An electromagnet is positioned on the first object a first distance from the joint, and a magnetic sensor is positioned on the second object a second distance from the joint. The magnetic sensor generates an output indicative of magnetic forces sensed by the magnetic sensor. Power supplied to the electromagnet is cycled during a monitoring session in accordance with a periodic schedule of alternating power-on periods and power-off periods. The electromagnet generates a magnetic field having a known north pole orientation during the power-on periods. A function is applied to the output of the magnetic sensor associated with at least one of the power-off periods that is associated with two consecutive periods of the power-off periods to generate a power-off value. The power-off value is subtracted from the output generated during the power-on period occurring between the two consecutive periods, wherein a modified output is generated. For each of power-on period occurring during the monitoring session, a distance between the electromagnet and the magnetic sensor is determined using the first distance, the second distance, the known north pole orientation, and the modified output. The distance and the known north pole orientation are indicative of relative positions of the first object and the second object.

In accordance with another embodiment of the present invention, a method is provided for monitoring relative positions of two objects sharing a common joint during motion between the two objects. The joint is one that supports relative motion between a first object coupled to the joint and a second object coupled to the joint. An electromagnet is positioned on the first object a first distance from the joint wherein poles of the electromagnet are at known orientations. A magnetic sensor is positioned on the second object a second distance from the joint, wherein the magnetic sensor generates an output indicative of magnetic forces sensed by the magnetic sensor. Power is supplied to the electromagnet during a monitoring session in accordance with a schedule of alternating-polarity periods, wherein the electromagnet generates a corresponding schedule of alternating-polarity magnetic fields. A function is applied to the output of the magnetic sensor associated with two consecutive periods of the alternating-polarity periods to generate a value. The value is subtracted from the output generated during a positive polarity period of the two consecutive periods, wherein a modified output is generated. For each positive polarity period of two consecutive periods occurring during the monitoring session, a distance between the electromagnet and the magnetic sensor is determined using the first distance, the second distance, the known orientations of the poles, and the modified output. The distance and the known orientations of the poles are indicative of relative positions of the first object and the second object.

BRIEF DESCRIPTION OF THE DRAWINGS

The summary above, and the following detailed description, will be better understood in view of the drawings that depict details of preferred embodiments.

DETAILED DESCRIPTION OF THE INVENTION

Figure 1:
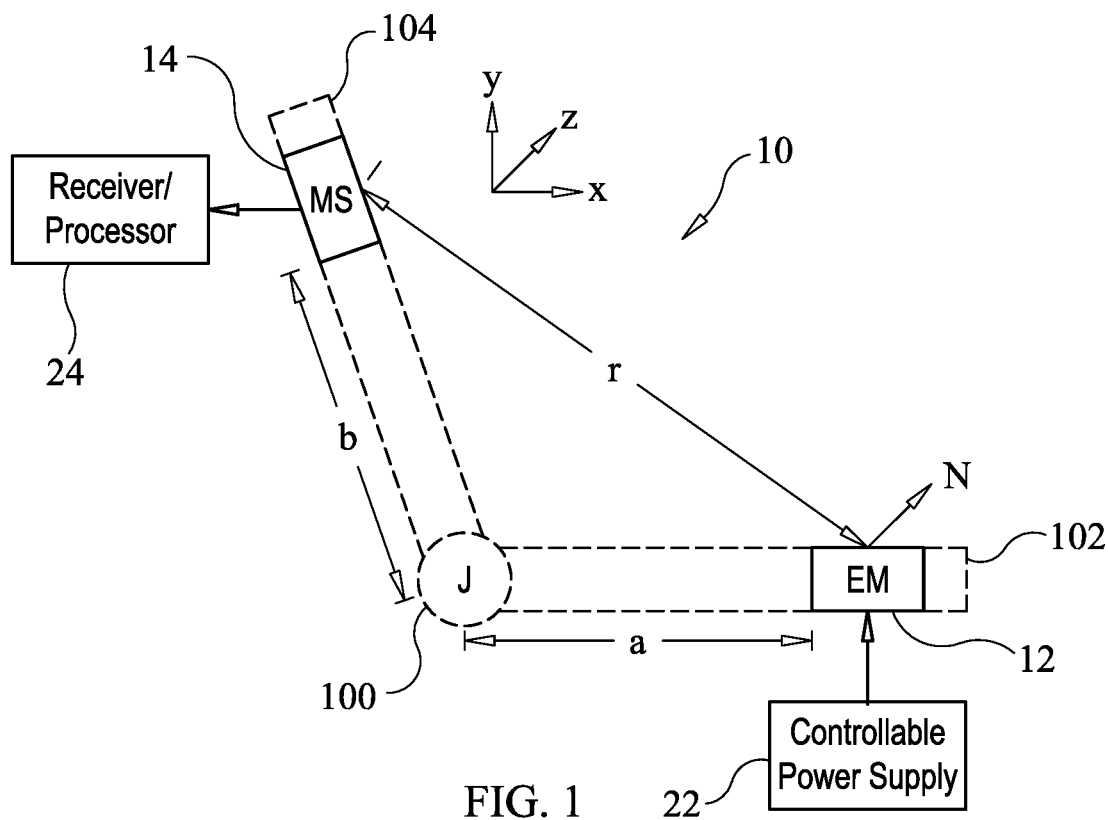
FIG. 1 is a schematic view of a magnetic-based system for monitoring relative positions of two objects sharing a common joint to indicate motion between the two objects in accordance with an embodiment of the present invention.

Referring now to the drawings and more particularly to FIG. 1, a schematic view of a magnetic-based system for monitoring relative positions of two objects sharing a common joint during motion between the two objects is shown and is referenced generally by numeral 10. By way of a non-limiting illustrative example, system 10 will be described for use with a living being such that the common joint is an anatomical joint supporting motion between two anatomical parts. As will be described further below, the two objects can move in accordance with a single degree of freedom or multiple degrees of freedom without departing from the scope of the present invention. The two objects and their common joint are not part of the present invention and do not limit the present invention. Accordingly, for clarity of illustration, the common joint ("J") 100 and the two objects 102 and 104 coupled to joint 100 are illustrated using dashed lines.

System 10 includes an electromagnet ("EM") 12 mounted on object 102 and at least one magnetic sensor ("MS") 14 mounted on object 104. Electromagnet 12 and magnetic sensor 14 can be mounted directly or indirectly on objects 102 and 104, respectively, without departing from the scope of the present invention. In general, electromagnet 12 and magnetic sensor 14 are considered to be mounted on their respective objects when they are positioned and maintained in a fixed relationship to one another and to common joint 100. Accordingly, electromagnet 12 and magnetic sensor 14 can be affixed directly to their respective object, or can be indirectly positioned on their respective object using a mounting system as will be explained further below.

Electromagnet 12 is powered by a controllable power supply 22. When energized, electromagnet 12 generates a three-dimensional magnetic field in the environment surrounding the electromagnet as is well-understood in the art. The orientation of the north-south poles (for example, the orientation of north ("N") is shown) of electromagnet 12 are dependent on the physical orientation of the electromagnet and the polarity of the power being supplied thereto. In general, the physical orientation of electromagnet 12 relative to object 102 will remain constant throughout a monitoring session. Electromagnet 12 is located a distance "a" from joint 100 where the value of "a" will frequently be known.

Magnetic sensor 14 is any of a variety of such sensors that can sense magnetic field strength along each of three axes defined by, for example, an x-y-z coordinate system. Such magnetic sensors are well-known in the art. The three-dimensional magnetic field strength data sensed by magnetic sensor 14 is supplied to a receiver/processor 24. Magnetic sensor 14 is located a distance "b" from joint 100 where the value of "b" will frequently be known. The distance values "a" and "b" can be the same or different without departing from the scope of the present invention.

Figure 2:
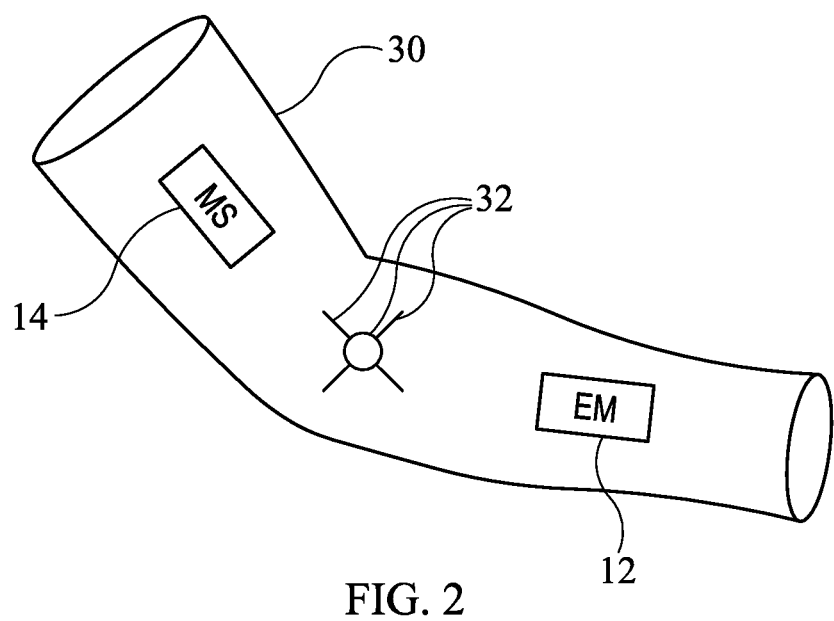
FIG. 2 is a schematic view of a flexible support sleeve used for the mounting of an electromagnet and a magnetic sensor in accordance with an embodiment of the present invention.

To facilitate optimal positioning (e.g., determined empirically) of electromagnet 12 and magnetic sensor(s) 14 on the objects being monitored, electromagnet 12 and magnetic sensor 14 can be mounted on a non-magnetic support (not shown in FIG. 1) that is adapted for optimal placement/positioning on objects 102/104 relative to joint 100. For example, when objects 102/104 and joint 100 are part of an anatomical appendage or limb (e.g. foot/leg and ankle; lower/upper leg and knee; hand/lower arm and wrist; lower arm/upper arm and elbow; etc.), the support can be a sleeve 30 as illustrated in FIG. 2 that fits over objects 102/104 and joint 100. Electromagnet 12 and magnetic sensor 14 are positioned on sleeve 30 such that a portion of sleeve 30 spans the common joint thereby essentially mounting electromagnet 12 on object 102 and mounting magnetic sensor 14 on object 104. Sleeve 30 must be flexible so as not to impede the relative motion of objects 102/104 about joint 100. Sleeve 30 could be made of elastic materials to facilitate its placement/positioning or could be held in place using, for example, straps (not shown) without departing from the scope of the present invention. Sleeve 30 can incorporate one or more indicators 32 used to properly position sleeve 30 relative to joint 100 to thereby facilitate the desired positioning of electromagnet 12 and magnetic sensor 14 for a particular application. Indicators 32 can include markings, cut-outs, three-dimensional relief elements, etc. without departing from the scope of the present invention.

Figure 3:
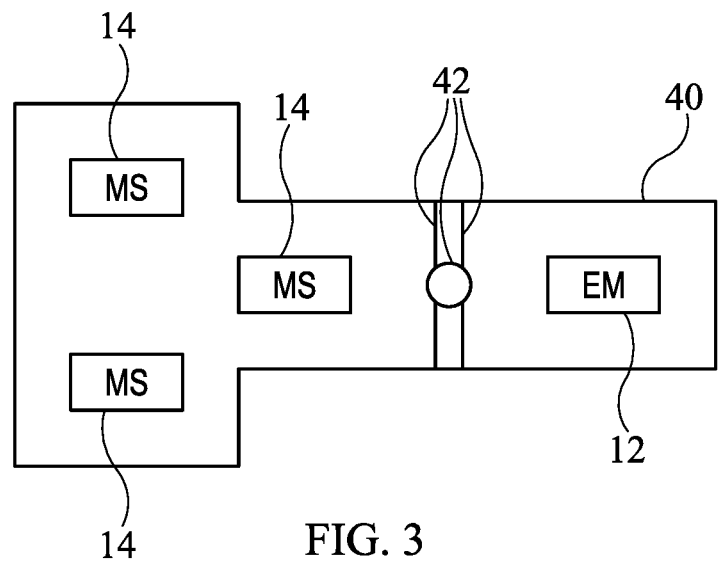
FIG. 3 is a schematic view of a flexible support used for the mounting of an electromagnet and multiple magnetic sensors in accordance with another embodiment of the present invention.

For applications that do not lend themselves to having a sleeve placed thereon (e.g., monitoring of shoulder, hip, spine, etc.), a flexible support used in the present invention can be generally or specifically-shaped piece of non-magnetic and flexible material. For example, FIG. 3 illustrates a flexible support 40 having electromagnet 12 and three spaced-apart magnetic sensors 14 positioned thereon. It is to be understood that the illustrated shape of support 40 and the positioning of electromagnet 12 and one or more magnetic sensors 14 are exemplary and do not represent limitations of the present invention. Markings 42 can be provided on an exposed face of support 40 to facilitate proper positioning of support 40 relative to a common joint for a particular application. Once positioned, a portion of support 40 between the electromagnet and magnetic sensor(s) spans the common joint. The opposing face of support 40 (not visible in FIG. 3) can include an adhesive that facilitates coupling of support 40 to a patient's skin. Regardless of how electromagnet 12 and magnetic sensor(s) 14 are positioned on the objects that coupled to a common joint to be monitored, the novel monitoring approach of the present invention remains the same.

Magnetic field sensors used for sensor 14 can generally be any commercially-available sensor that can sense magnetic fields. As is known in the art, such sensors provide for large scale sensing of the Earth's magnetic field, magnetic anomalies, orientation, and distance. Unfortunately, these attributes also make magnetic field sensors susceptible to magnetic interference from the Earth's magnetic field, the environment, and nearby ferrous objects. The interference can alter the magnetic field sensor's reading to the point that the reading is unreliable. Approaches typically used to protect a sensor from this magnetic interference include, but are not limited to, using a hardware shield, using a field-producing magnet that is strong enough to eclipse all other fields, or using multiple magnetic sensors. Using a hardware shield can be problematic as it can interfere with the magnetic fields that are supposed to be read or even become magnetized itself. Strong field-producing magnets become problematic in small measurement environments. The use of multiple sensors generally increases the hardware footprint needed for a sensing application.

Research in the field of magnetic-based systems/methods to measure body motion does not account for the influence of environmental interference. This leads to the drawback that any change in a magnetic field reading could be interpreted as a change in body motion. As will be explained further below, the present invention removes magnetic interference so that any change in magnetic field reading is purified in that it only results from a change in the localization of the field-producing electromagnet 12.

The problem with using an electromagnet and magnetic sensor combination for dynamic motion monitoring is the sensor's above-described susceptibility to outside magnetic fields that can include, but are not limited to, the magnetic field of the Earth, ferrous metal objects near the monitoring location, and other magnetized objects near the monitoring location. The outside magnetic fields create a noisy signal that can make it hard to distinguish the movement of electromagnet 12 from the change in surrounding magnetic fields being sensed by magnetic sensor 14. To deal with this problem, the present invention continually eliminates the surrounding and changing environmentally-created magnetic field from the reading of magnetic sensor 14 during a monitoring session. Briefly, this is accomplished by controlling the electromagnet's operation (e.g., turning the electromagnet on and off at a high frequency, or changing the electromagnet's polarity at a high frequency), and then applying a dynamically-updated function to the magnetic sensor's output throughout a monitoring session to eliminate the interfering magnetic field data from the magnetic sensor's output.

Figure 4:
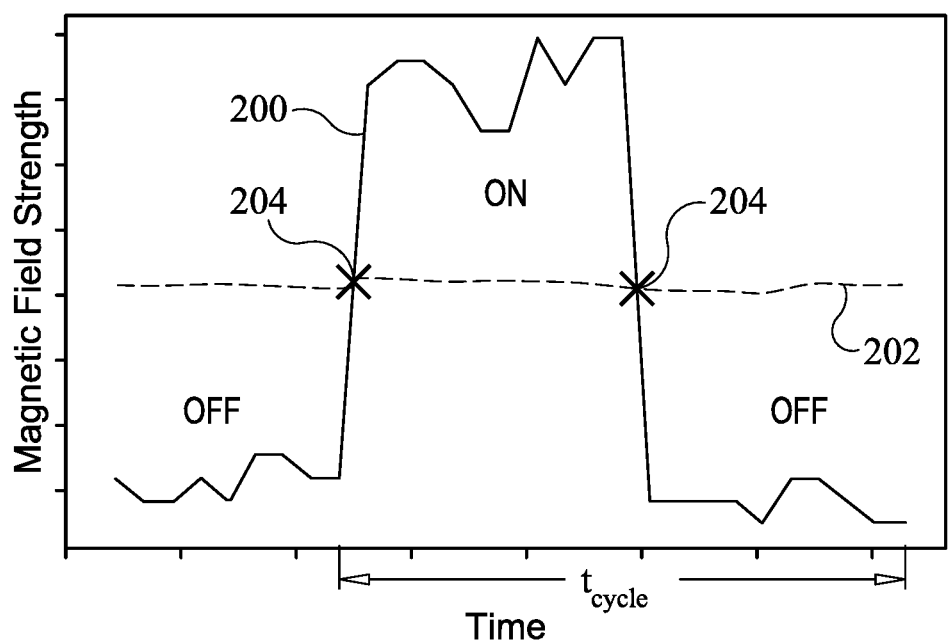
FIG. 4 is a graph of the magnetic field strength as a function of time for the ON/OFF states of an electromagnet in accordance with an embodiment of the present invention.

In one embodiment of the present invention that cycles power to electromagnet 12, the output of electromagnet 12 is characterized by two states: ON and OFF. When electromagnet 12 is ON, magnetic sensor 14 senses the combination of the magnetic field produced by electromagnet 12 and the magnetic field of the surrounding environment whose contributions can change with time and/or movement of magnetic sensor 14. When electromagnet 12 is OFF, magnetic sensor 14 only senses the magnetic field of the surrounding environment. The sensed magnetic field strength as a function of time associated with these two states is illustrated generally by curve 200 in FIG. 4. As would be understood by one of ordinary skill in the art, the variations in magnetic field strength occurring during ON and OFF periods is due to error of the magnetic sensor reading the magnetic field. Furthermore, the slope of curve 200 between ON and OFF states would be vertical in an ideal world, but will have a slight slope (as illustrated) due to magnetic sensor sampling rates.

Using curve 200, a time cycle ($t_{cycle}$) is defined that is the total time of a single ON state followed by a single OFF state. The total time spent in the ON state can be equal to or different than the total time spent in the OFF state within each $t_{cycle}$. The electromagnet's cycling rate is defined as the number of times $t_{cycle}$ occurs per second. For every ON and OFF state, there is a beginning and an end. To find these points, an average magnetic field strength is determined and is indicated by line 202 in FIG. 4. The average indicated by line 202 is generated using the magnetic field strength data points in one time cycle. Each time the magnetic sensor's reading (i.e., curve 200) crosses average line 202 as indicated by crosses 204, the point immediately before a cross 204 is an end of an ON state and the point immediately after a cross 204 is a beginning of an ON state.

To eliminate the magnetic field contributions from the surrounding environment, one embodiment of the present invention determines the average of two OFF states occurring immediately before and after an ON state. By generating an average using OFF-state magnetic field strength data immediately before and immediately after an ON state, the present invention adapts to rapid changes in a magnetic field environment that can occur during a motion monitoring session, i.e., changes occurring during the OFF states that immediately precede and proceed an ON state. It is to be understood that the present invention is not limited to an averaging function. For example, if the monitoring environment caused changes in the ON/OFF states, a linear or quadratic regression function could be used to estimate the differences between the ON and OFF states at any given time. Further, the present invention may not need to use all of preceding/following OFF states. For example, in cases where the duration of an OFF state is equal to the duration of an ON state, it may be sufficient to use the second half of an OFF state immediately preceding an ON state and the first half of an OFF state immediately following an ON state. In general, the portions of an OFF state immediately preceding and following an ON state should be long enough to provide a good estimate of the OFF state. While the use of at least portions of immediately preceding/following OFF states provides the most accurate data, some applications could make use of just an immediately preceding OFF state or just an immediately following OFF state without departing from the scope of the present invention.

The generated OFF-state average value is subtracted from the ON-state magnetic field strength occurring between the two OFF states used to generate the OFF-state average value. A result of the modified ON-state magnetic field strength represents a response that is due solely to the magnetic field produced by electromagnet 12. The above-described average generation and subtraction is performed for each ON state of a monitoring session. The above-described process is performed in three-dimensions, e.g., in all three x, y, z axes of a Cartesian coordinate system.

Monitoring motion between objects 102 and 104 essentially requires determining relative positions of the two objects at multiple points in time during a measurement session. In the present invention, this is accomplished by localization of electromagnet 12 that determines the distance "r" (FIG. 1) between electromagnet 12 and magnetic sensor 14 for each of the ON states of electromagnet 12 occurring during a monitoring session. Distance "r" along with the known north pole orientation of electromagnet 12 are then readily used to unambiguously indicate the relative positions of objects 102 and 104. Briefly, distance "r" is readily determined for each ON state using distances "a" and "b", the known north pole orientation of electromagnet 12, and the ON state's modified magnetic field strength described above. Details of the electromagnet localization process will be described further below.

For any reading recorded by magnetic sensor 14, there is a set of location and orientation pairs for electromagnet 12. The description to follow discusses the relationship between a magnetic sensor reading and orientation of the electromagnet, explains how to calculate a single location and orientation pair of the electromagnet, and discusses the entirety of the set of location and orientation pairs for the electromagnet.

Figure 5:
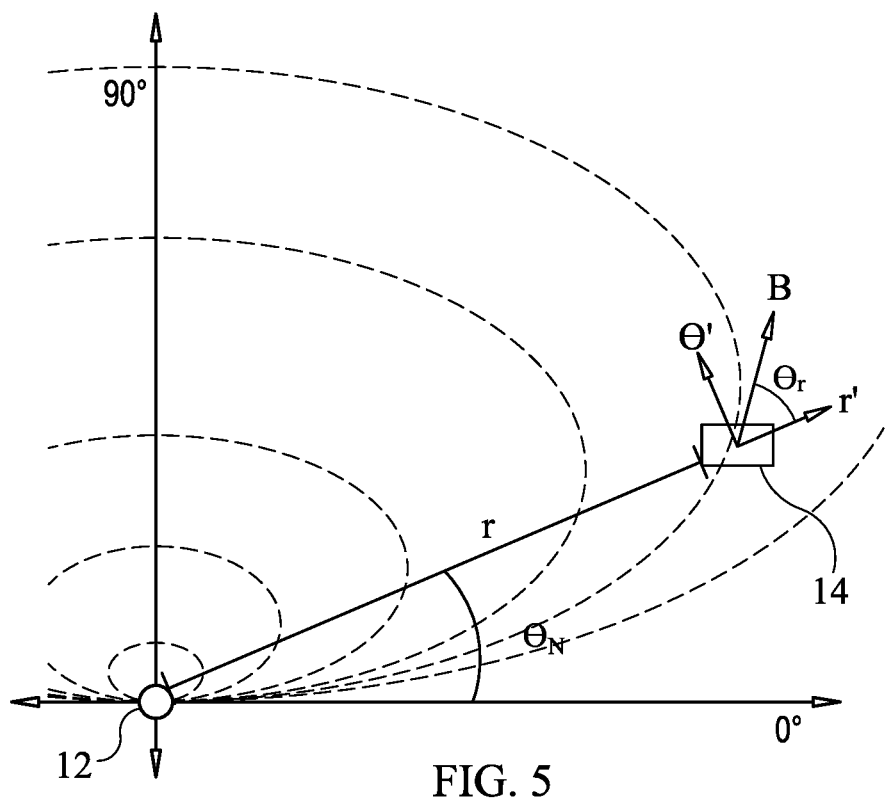
FIG. 5 is a two-dimensional graphic representation of the magnetic field produced by an electromagnet from the perspective of the electromagnet.

Magnets are described as dipoles, with one end of a magnet being a north pole and the other being a south pole. The opposite poles attract one another, and identical poles repel each other. Electromagnets are magnets with adjustable strength that can be turned on and off. A generalized two-dimensional representation of the magnetic field surrounding and from the perspective of electromagnet 12 is shown by the dotted lines in FIG. 5. As is known in the art, a three-dimensional representation would show this same magnetic field rotated around electromagnet 12. This means that rotating electromagnet 12 would not change the magnetic field reading.

Magnetic fields around a magnet can be modeled given a magnet's strength with the assumption that a magnet is a perfect dipole. For any location around electromagnet 12, magnetic sensor 14 reads a magnetic field "B" that reflects the distance "r" and angle $\theta_N$ from the north pole of the electromagnet. Since magnetic fields depend heavily on the angle $\theta_N$, polar coordinates can be used to describe the magnetic field reading. The direction from electromagnet 12 to magnetic sensor 14 is represented as r' and the direction perpendicular to direction r' is θ'. So, given a distance r and angle $\theta_N$, the magnetic field B at the location (r,$\theta_N$) can be represented with the following polar equation:

$$B(r;\theta_N) = (\mu_0|m|)/(4\pi r^3) * (2\cos\theta_N r' + \sin\theta_N \theta') \quad (1)$$

where B is the magnetic field strength at the center of the electromagnet's core in Teslas, r is the distance from electromagnet 12 to magnetic sensor 14, $\theta_N$ is the angle of the north of electromagnet 12, $\mu_0$ is a constant of magnetic permeability of free space or $4\pi*10^{-7}$,

|m| is the magnetic moment of electromagnet 12, i.e., (current*area of a single turn*number of turns), r' is the direction from electromagnet 12 to magnetic sensor 14, and θ' is the direction perpendicular to r'.

Figure 6:
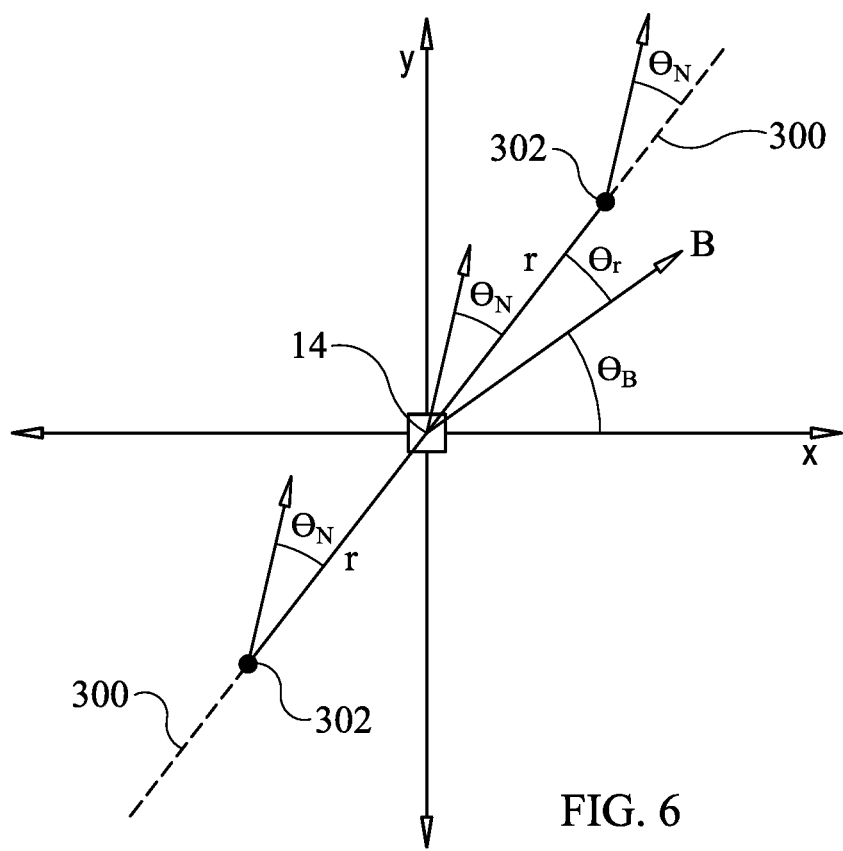
FIG. 6 is a two-dimensional graphic representation of the position of an electromagnet from the perspective of a magnetic sensor.

In the present invention, the distance r and orientation $\theta_N$ of electromagnet 12 are determined as will be explained below with reference to FIG. 6. With magnetic sensor 14 assumed to be located at the origin of the coordinate system, magnetic sensor 14 senses a magnetic field vector B. Given this reading, the angle $\theta_B$ between vector B and the x-axis can be calculated. Assuming that electromagnet 12 is somewhere on a line that goes through the origin (as represented by line 300 in FIG. 6), $\theta_r$ will be the angle between line 300 and vector B which can be calculated. Since $\theta_r$ is also the angle between B and r' in FIG. 5, the direction of the electromagnet's north can be calculated with the following equation:

$$\theta_N = \arctan(2\tan\theta_r) \quad (2)$$

where $\theta_N$ is the north for a magnet located anywhere on line 300. Knowing $\theta_N$, the electromagnet's north with respect to the x-axis ($\theta_x$) can be calculated as $$\theta_x = \theta_N + \theta_r + \theta_B \quad (3)$$

Next, the distance r is determined via a derivation of Equation (1) where $$r = [(\mu_0|m|)/(4\pi r^3) * (4\cos^2\theta_N + \sin^2\theta_N)^{1/2}]^{1/3} \quad (4)$$

Figure 7:
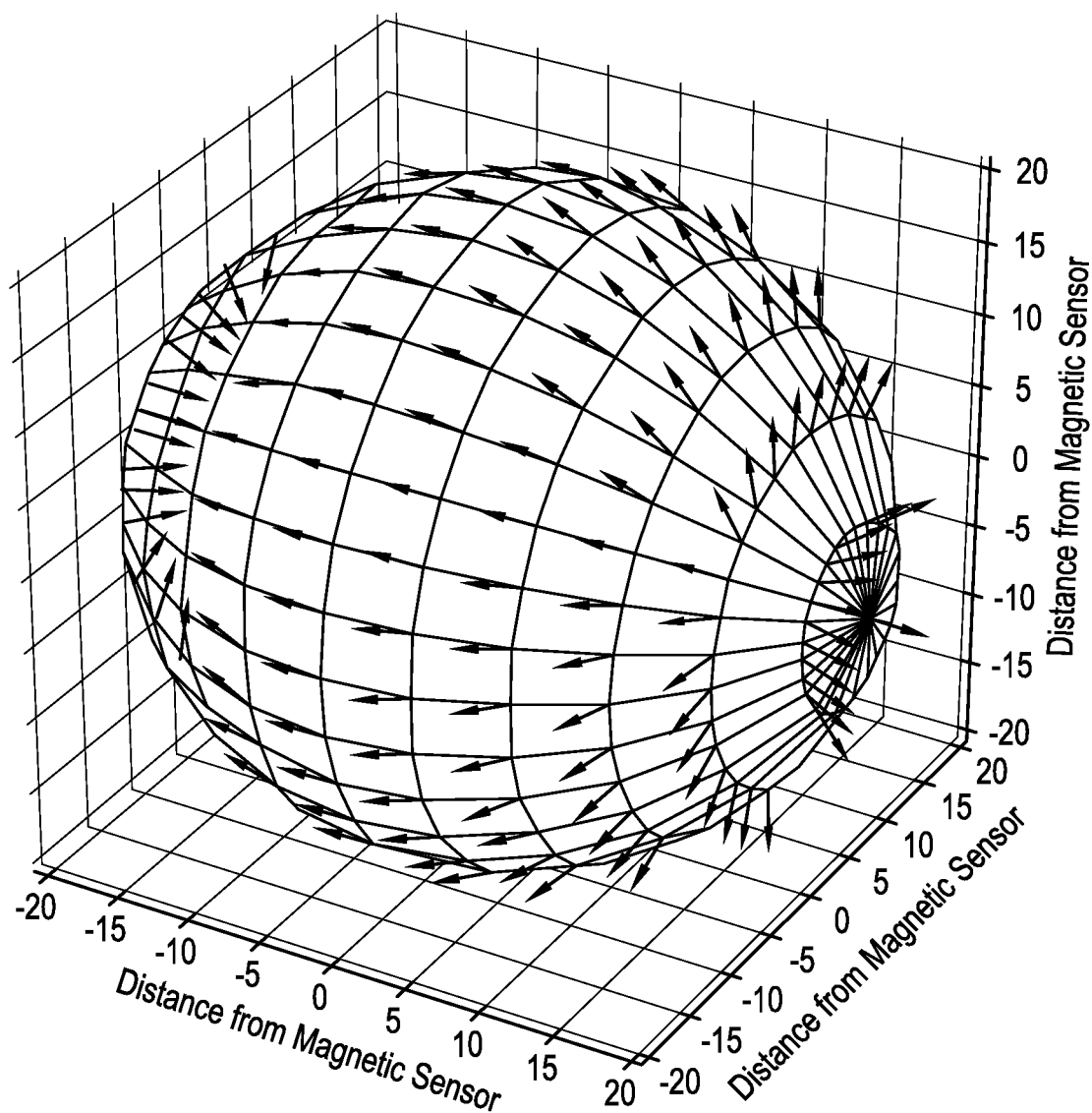
FIG. 7 is a graphical representation of an ellipsoid of possible electromagnet locations and orientations.

This value of r is the distance away from the coordinate system's origin on line 300 where electromagnet 12 is located. That is, electromagnet 12 can be located in two locations denoted by the points 302 on line 300 as shown in FIG. 6. The above process is repeated for every possible line through the coordinate system's origin to thereby yield a set of location and orientation pairs around magnetic sensor 14 in the shape of an ellipsoid as shown in FIG. 7. In the illustrated example, the ellipsoid illustrating the magnetic field is pointed in the positive x direction on the same coordinate system as that of the magnetic sensor.

The present invention can be used in many different application scenarios that require monitoring of relative positions of two objects sharing a common joint during motion between the two objects throughout the course of a monitoring session. In each application, the key metrics determined by the present invention are distance between the electromagnet and magnetic sensor, and the orientation of the electromagnet. The same approach is used for joints supporting single-degree-of-freedom motion and three-degree-of-freedom motion. In each case, a model for the joint to be monitored is used to describe joint motion. As mentioned above, the present invention is well-suited to monitoring body motion where the electromagnet and magnetic sensor are positioned on different body parts that share a common joint. Then, because biomechanics of the joint are known, the exact localization of the electromagnet can be determined thereby permitting the monitoring of joint angles, speed of motion, and even gestures.

As mentioned above, control of the electromagnet's operation is not limited to cycling power to the electromagnet at a high frequency. For example, rather than cycling power to the electromagnet, the electromagnet's polarity can be alternated or flipped back-and-forth at a high frequency. That is, in this embodiment, power can be supplied continuously to the electromagnet in accordance with a schedule of alternating polarities. A primary advantage of this approach is that an electromagnet's output can be changed at a faster rate when changing or flipping polarity as opposed to changing between ON and OFF states. As a result, polarity flipping could be used to allow the present invention to be adapted for faster object motions. In addition, polarity flipping provides a more distinct change in a generated magnetic field that could allow the system's magnetic sensor to be located further from the electromagnet as compared to the case where power to the electromagnet is cycled.

For the alternating-polarity approach, magnetic field contributions from the surrounding environment are eliminated by, for example, determining an average of a consecutive alternating-polarity period pair, e.g., a "negative" polarity period and its immediately following "positive" polarity period, or a "positive" polarity period and its immediately following "negative" polarity period. Similar to the cycled power embodiment, the generated average value is subtracted from the magnetic field strength sensed during the positive polarity period of two consecutive periods. The above-described average generation and subtraction is performed for each consecutive alternating-polarity period pair during a monitoring session. The above-described process is performed in three-dimensions, e.g., in all three x, y, z axes of a Cartesian coordinate system.

In another embodiment of the present invention, multiple electromagnets could be employed along with a single magnetic sensor. For this type of embodiment, each electromagnet could be controlled such that the generated magnetic fields could be distinguished at the magnetic sensor. In one scenario, the generated magnetic fields could "non-interfering" as would be the case when the electromagnets were timed to prevent interference (e.g., if there were two electromagnets, one could be ON from 0.1 sec to 0.2 sec while the other could be ON from 0.2 sec to 0.3 sec, and both of them could be OFF from 0.3 to 0.4 sec). In another scenario, the generated magnetic field could be "interfering" but have different cycling rates (e.g., if one electromagnet was cycled at 10 times a second, and the other was cycled at 100 times a second). The strength of the magnetic fields generated from each of the electromagnets could be distinguished based on cycling rate even though they interfered with each other. That is, knowledge of the cycling rates provides the ability to detect which electromagnet contributes to the amount of field strength.

The advantages of the present invention are numerous. The magnetic-based method and system can be used to accurately monitor motion of two objects sharing a common joint in a dynamically changing environment. The combination of an electromagnet and magnetic sensor is used to eliminate environmental magnetic interference from a magnetic field reading. The resulting purified reading provides for accurate localization of the electromagnet with respect to the magnetic sensor during a motion monitoring session.

INCORPORATION BY REFERENCE

All publications, patents, and patent applications cited herein are hereby expressly incorporated by reference in their entirety and for all purposes to the same extent as if each was so individually denoted.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

We claim:

1. A method for monitoring relative positions of two objects sharing a common joint during motion between the two objects, comprising the steps of:
    providing a joint that supports relative motion between a first object coupled to the joint and a second object coupled to the joint;
    positioning an electromagnet on the first object a first distance from the joint;
    positioning a magnetic sensor on the second object a second distance from the joint, wherein the magnetic sensor generates an output indicative of magnetic forces sensed by the magnetic sensor;
    cycling power to the electromagnet during a monitoring session in accordance with a periodic schedule of alternating power-on periods and power-off periods, wherein the electromagnet generates a magnetic field having a known north pole orientation during said power-on periods;
    applying a function to the output of the magnetic sensor associated with at least one of said power-off periods that is associated with two consecutive periods of said power-off periods to generate a power-off value;
    subtracting said power-off value from the output generated during one of said power-on periods occurring between said two consecutive periods, wherein a modified output is generated; and
    determining, for each of said power-on periods occurring during said monitoring session, a distance between the electromagnet and the magnetic sensor using the first distance, the second distance, the known north pole orientation, and said modified output associated therewith, wherein said distance and the known north pole orientation are indicative of relative positions of the first object and the second object.

2. A method according to claim 1, wherein said function comprises an averaging function.

3. A method according to claim 1, wherein a duration of each of said power-off periods is equal to a duration of each of said power-on periods.

4. A method according to claim 1, wherein a duration of said two consecutive periods is at least as long as a duration of said one of said power-on periods occurring between said two consecutive periods.

5. A method according to claim 1, wherein said steps of positioning include the steps of:
    providing a flexible support; and
    coupling the electromagnet and the magnetic sensor to the flexible support in a spaced-apart relationship, wherein a portion of the flexible support between the electromagnet and the magnetic sensor spans the joint after said steps of positioning are complete.

6. A method according to claim 5, wherein said steps of positioning further include the steps of:
    providing an indicator on the flexible support between the electromagnet and the magnetic sensor; and
    aligning the indicator with the joint.

7. A method according to claim 1, wherein said first distance and said second distance are known.

8. A method according to claim 1, further comprising the step of positioning additional magnetic sensors on the second object.

9. A method according to claim 1, further comprising the step of positioning additional electromagnets on the first object.

10. A method for monitoring relative positions of two objects sharing a common joint during motion between the two objects, comprising the steps of:
    providing a joint that supports relative motion between a first object coupled to the joint and a second object coupled to the joint;
    providing a flexible support having an electromagnet and a magnetic sensor coupled to the flexible support in a spaced-apart relationship, wherein the magnetic sensor generates an output indicative of magnetic forces sensed by the magnetic sensor;
    coupling the flexible support to the first object and the second object, wherein the electromagnet is positioned on the first object a first distance from the joint, and wherein the magnetic sensor is positioned on the second object a second distance from the joint;
    cycling power to the electromagnet during a monitoring session in accordance with a periodic schedule of alternating power-on periods and power-off periods, wherein the electromagnet generates a magnetic field having a known north pole orientation during said power-on periods;
    applying an averaging function to the output of the magnetic sensor associated with two consecutive periods of said power-off periods to generate a power-off value;
    subtracting said power-off value from the output generated during one of said power-on periods occurring between said two consecutive periods, wherein a modified output is generated; and
    determining, for each of said power-on periods occurring during said monitoring session, a distance between the electromagnet and the magnetic sensor using the first distance, the second distance, the known north pole orientation, and said modified output associated therewith, wherein said distance and the known north pole orientation are indicative of relative positions of the first object and the second object.

11. A method according to claim 10, wherein a duration of each of said power-off periods is equal to a duration of each of said power-on periods.

12. A method according to claim 10, wherein a duration of said two consecutive periods is at least as long as a duration of said one of said power-on periods occurring between said two consecutive periods.

13. A method according to claim 10, further comprising the steps of:
providing an indicator on the flexible support between the electromagnet and the magnetic sensor; and
aligning the indicator with the joint during said step of coupling.

14. A method according to claim 10, wherein said first distance and said second distance are known.

15. A method according to claim 10, wherein additional magnetic sensors are provided on the flexible support.

16. A method according to claim 10, wherein additional electromagnets are provided on the flexible support.

17. A method for monitoring relative positions of two objects sharing a common joint during motion between the two objects, comprising the steps of:
providing a joint that supports relative motion between a first object coupled to the joint and a second object coupled to the joint;
positioning an electromagnet on the first object a first distance from the joint wherein poles of the electromagnet are at known orientations;
positioning a magnetic sensor on the second object a second distance from the joint, wherein the magnetic sensor generates an output indicative of magnetic forces sensed by the magnetic sensor;
supplying power to the electromagnet during a monitoring session in accordance with a schedule of alternating-polarity periods, wherein the electromagnet generates a corresponding schedule of alternating-polarity magnetic fields;
applying a function to the output of the magnetic sensor associated with two consecutive periods of said alternating-polarity periods to generate a value;
subtracting said value from the output generated during a positive polarity period of said two consecutive periods, wherein a modified output is generated; and
determining, for each said positive polarity period of said two consecutive periods occurring during said monitoring session, a distance between the electromagnet and the magnetic sensor using the first distance, the second distance, the known orientations of the poles, and said modified output associated therewith, wherein said distance and the known orientations of the poles are indicative of relative positions of the first object and the second object.

18. A method according to claim 17, wherein said function comprises an averaging function.

19. A method according to claim 17, wherein said steps of positioning include the steps of:
providing a flexible support; and
coupling the electromagnet and the magnetic sensor to the flexible support in a spaced-apart relationship, wherein a portion of the flexible support between the electromagnet and the magnetic sensor spans the joint after said steps of positioning are complete.

20. A method according to claim 19, wherein said steps of positioning further include the steps of:

providing an indicator on the flexible support between the electromagnet and the magnetic sensor; and
aligning the indicator with the joint.

21. A method according to claim 17, wherein said first distance and said second distance are known.

22. A method according to claim 17, further comprising the step of positioning additional magnetic sensors on the second object.

23. A method according to claim 17, further comprising the step of positioning additional electromagnets on the first object.

24. A system for monitoring relative positions of two objects sharing a common joint during motion between the two objects, comprising:
a flexible support;
an electromagnet coupled to said flexible support;
a magnetic sensor coupled to said flexible support in a spaced-apart relationship with respect to said electromagnet, wherein said magnetic sensor generates an output indicative of magnetic forces sensed by said magnetic sensor;
said flexible support adapted to be coupled a first object and a second object wherein the first object and the second object are coupled to a common joint, wherein said electromagnet is adapted to be positioned on the first object a first distance from the common joint, and wherein said magnetic sensor is adapted to be positioned on the second object a second distance from the common joint;
a power source for cycling power to said electromagnet during a monitoring session in accordance with a periodic schedule of alternating power-on periods and power-off periods, wherein said electromagnet generates a magnetic field having a known north pole orientation during said power-on periods; and
a processor coupled to said magnetic sensor for
applying a function to said output of said magnetic sensor associated with at least one of said power-off periods that is associated with two consecutive periods of said power-off periods to generate a power-off value,
subtracting said power-off value from the output generated during one of said power-on periods occurring between said two consecutive periods, wherein a modified output is generated, and
determining, for each of said power-on periods occurring during said monitoring session, a distance between said electromagnet and said magnetic sensor using said first distance, said second distance, said known north pole orientation, and said modified output associated therewith, wherein said distance and said known north pole orientation are indicative of relative positions of the first object and the second object.

25. A system as in claim 24, wherein said function comprises an averaging function.

26. A system as in claim 24, wherein a duration of each of said power-off periods is equal to a duration of each of said power-on periods.

27. A system as in claim 24, wherein a duration of said two consecutive periods is at least as long as a duration of said one of said power-on periods occurring between said two consecutive periods.

28. A system as in claim 24, wherein said flexible support includes an alignment indicator between said electromagnet and said magnetic sensor, said alignment indicator adapted to be aligned with the common joint.

29. A system as in claim 24, wherein said first distance and said second distance are known.

30. A system as in claim 24, further comprising additional magnetic sensors coupled to said flexible support.

31. A system as in claim 24, further comprising additional electromagnets coupled to said flexible support.

32. A system as in claim 24, wherein said flexible support comprises a flexible sleeve.

* * * * *